United States Patent

Marcovecchio et al.

[11] Patent Number: 5,346,381
[45] Date of Patent: * Sep. 13, 1994

[54] APPARATUS FOR PREPARATION OF SAMPLES FOR SPECTROGRAPHIC ANALYSIS

[75] Inventors: Joseph Marcovecchio, Berkeley Heights; Joseph K. Katzenberger, Lebanon, both of N.J.

[73] Assignee: Instruments SA, Inc., Edison, N.J.

[*] Notice: The portion of the term of this patent subsequent to Mar. 30, 2010 has been disclaimed.

[21] Appl. No.: 952,263

[22] Filed: Sep. 28, 1992

Related U.S. Application Data

[62] Division of Ser. No. 647,419, Jan. 29, 1991, Pat. No. 5,198,241.

[51] Int. Cl.⁵ .............................................. B29C 43/00
[52] U.S. Cl. ................................ 425/149; 91/362; 100/51; 251/322; 425/167; 425/170
[58] Field of Search .................... 91/362; 100/48, 50, 100/51, 52; 137/624.11; 251/322; 264/40.5; 425/78, 149, 167, 170, 406

[56] References Cited

U.S. PATENT DOCUMENTS

| | | | |
|---|---|---|---|
| 1,980,752 | 11/1934 | Eskilson et al. | 251/322 |
| 3,098,501 | 7/1963 | McLeod | 251/322 |
| 3,250,294 | 5/1966 | Hipple | 137/624.11 |
| 3,330,003 | 7/1967 | Eggenberger et al. | 425/170 |
| 3,559,247 | 2/1971 | Larsson | 425/170 |
| 3,652,053 | 3/1972 | Poltras et al. | 251/322 |
| 4,085,768 | 4/1978 | Norr | 137/624.11 |
| 4,221,236 | 9/1980 | Rosenberg | 137/624.11 |
| 4,777,798 | 10/1988 | Jacobson et al. | 91/362 |
| 4,911,192 | 3/1990 | Hartfiel et al. | 137/624.11 |
| 5,198,241 | 3/1993 | Marcovecchio et al. | 425/149 |

*Primary Examiner*—Charles S. Bushey
*Attorney, Agent, or Firm*—Handal & Morofsky

[57] ABSTRACT

An apparatus for compressing a workpiece is disclosed. The apparatus has a die to receive the workpiece in powdered or other form. An abutment holds the workpiece in a fixed position against the application of force, while a hydraulic cylinder is positioned to exert force against the die in the direction toward the abutment. A pump feeds hydraulic fluid to the hydraulic cylinder, and a pressure control valve is coupled to the hydraulic cylinder to control the maximum pressure in the hydraulic cylinder. The pressure control valve has a sealing member, a seat which engages the sealing member with the sealing member closing the outlet, a spring which urges the sealing member towards the seat, closing the outlet, and a backing member putting the spring under compression by maintaining a distance between the backing member and the seat. A stepping motor is rigidly mounted with respect to the seat. The stepping motor has a shaft which may be advanced towards and away from the valve seat whereby the degree of compression on the spring may be adjusted.

11 Claims, 4 Drawing Sheets

APPARATUS FOR PREPARATION OF SAMPLES FOR SPECTROGRAPHIC ANALYSIS

This application is a division, of application Ser. No. 07/647,419, filed Jan. 29, 1991, now U.S. Pat. No. 5,198,241.

TECHNICAL FIELD

The present invention relates to a process for forming a sample of a material into a uniform pellet for subjection to spectrographic analysis. Such analysis typically involves irradiating the sample with x-rays or other appropriate radiation and analyzing the spectra emitted in response thereto.

BACKGROUND

Current practice in x-ray Raman, fluorescence and other spectrographic methods involves the use of sample pelletization. The advantages of sample pelletization include 1) enhanced sample-to-sample uniformity, 2) increased density of sample material and, accordingly, increased strength of emitted radiation, 3) exclusion of contaminant materials, such as air (resulting in reduced spurious emissions on account of such contaminant materials), and 4) compaction of the sample into a single undispersable tablet resulting in greatly reduced contamination of the chamber within which the sample is irradiated.

Current systems for pelletizing samples for spectrographic analysis generally use a multi-part cylindrical die into which the material to be pelletized is loaded. The loaded die is then placed in a pelletizing apparatus for compaction of the sample.

Generally, a pelletizing apparatus comprises a hydraulically-operated platen and a fixed abutment. The loaded die is placed between the platen and the abutment and the user causes the apparatus to advance the platen toward the abutment, thus applying pressure to the die and compressing the sample within into a pellet. Desired pressures, often on the order of tons, are achieved by hydraulic means, with the desired pressure being realized by the pumping of hydraulic fluid in a hydraulic circuit. In accordance with current practice, when the desired pressure is reached, the operator of the apparatus is directed to stop the operation of the pump which causes the platen to advance toward the abutment, and maintain pressure for a desired period of time. The operator then slowly manually releases the pressure in the hydraulic system, which drives the platen, through the use of a hand operated valve.

In order to protect against damaging the die, the prior art pelletizing apparatus is generally provided with a pressure relief valve which may be manually set by the operator to a pressure which, even in the event of a malfunction or operator error, will be the maximum pressure to which the die will be subjected. Such pressure is generally keyed to the physical limits at which the die can be operated and will usually be higher than the actual operating pressure during the pelletizing process.

While the raising of pelletizing pressure to a desired value, holding for a desired time and release of pressure appears to be a simple and straight forward process; it actually has a number of problems which have been routinely tolerated for many years. For example, after the operation of the pump is stopped, often due to factors such as wear or the like, the pressure in the system will be slowly released. This affects the quality of the compacted sample because it has not been subjected to the desired high pressure for a long enough period of time. In addition, after the required pressing period has been undergone by the sample, it has been discovered in accordance with the invention, that the release of pressure through the actuation of the manual release valve, even in the case of highly skilled operators, often results in no change in applied pressure during an initial phase of the release and, as the valve continues to be opened wider, a relatively abrupt change in pressure. This abrupt change often results in fracturing of the pelletized sample, thus rendering it useless. One approach to this problem has been to set the pressure relief valve to the desired compacting pressure; however, this approach is clumsy and difficult to control.

SUMMARY OF THE INVENTION

The invention is intended to provide a remedy. It solves the problem of how to reliably obtain uniformly compressed sample pellets. At the same time, the inventive system and method provides for the pelletizing of samples without need for a skilled operator. In accordance with the invention, this is achieved by providing the system with a pressure relief valve whose set point is varied in response to operator commands inputted into a control circuit.

More particularly, the apparatus comprises a die to receive the workpiece in powdered or other form. An abutment holds the workpiece in a fixed position against the application of force, while a hydraulic cylinder is positioned to exert force against the die in the direction towards the abutment. A pump feeds hydraulic fluid to the hydraulic cylinder, and a pressure control valve is coupled to the hydraulic cylinder to control the maximum pressure in the hydraulic cylinder. The pressure control valve is comprised of a sealing member, a seat which defines an outlet that is configured, dimensioned and positioned to engage the sealing member while the sealing member closes the outlet, a spring which urges the sealing member towards the seat (closing the outlet), a backing member which puts the spring under compression by maintaining a distance between the backing member and the seat, and a mechanical structure which adjusts the distance.

The mechanical structure comprises a stepper motor rigidly mounted with respect to the seat. The stepper motor has a shaft which may be advanced toward and away from the valve seat whereby the degree of compression on the spring may be adjusted.

The apparatus further comprises means to detect the pressure of hydraulic fluid in the hydraulic cylinder and to control the stepper motor in response thereto.

A control circuit is programmed to cause the shaft of the stepping motor to pull away in a first direction from the seat by a first number of steps which is less than that needed to cause a change in pressure in the hydraulic cylinder and then proceed in the opposite direction a second number of steps smaller than the first number of steps and then go in the first direction the first number of steps. The control circuit is programmed to cause the shaft to alternately move in the first direction, the first number of steps and the second direction, the second number of steps, until pressure is reduced to a desired value.

The release of pressure by alternately advancing and retracting the shaft of the stepping motor may be done over a fixed period of time.

In accordance with a preferred embodiment of the invention, the set point of the pressure actuated valve is set using a precision stepper motor which advances its shaft linearly against a spring in the pressure actuated valve, thus varying the pressure necessary to actuate the pressure responsive function of the valve.

BRIEF DESCRIPTION OF THE DRAWINGS

One way of carrying out the invention is described in detail below with reference to drawings which illustrate only one specific embodiment of the invention and in which.

BEST MODE FOR CARRYING OUT THE INVENTION

Figure 1:
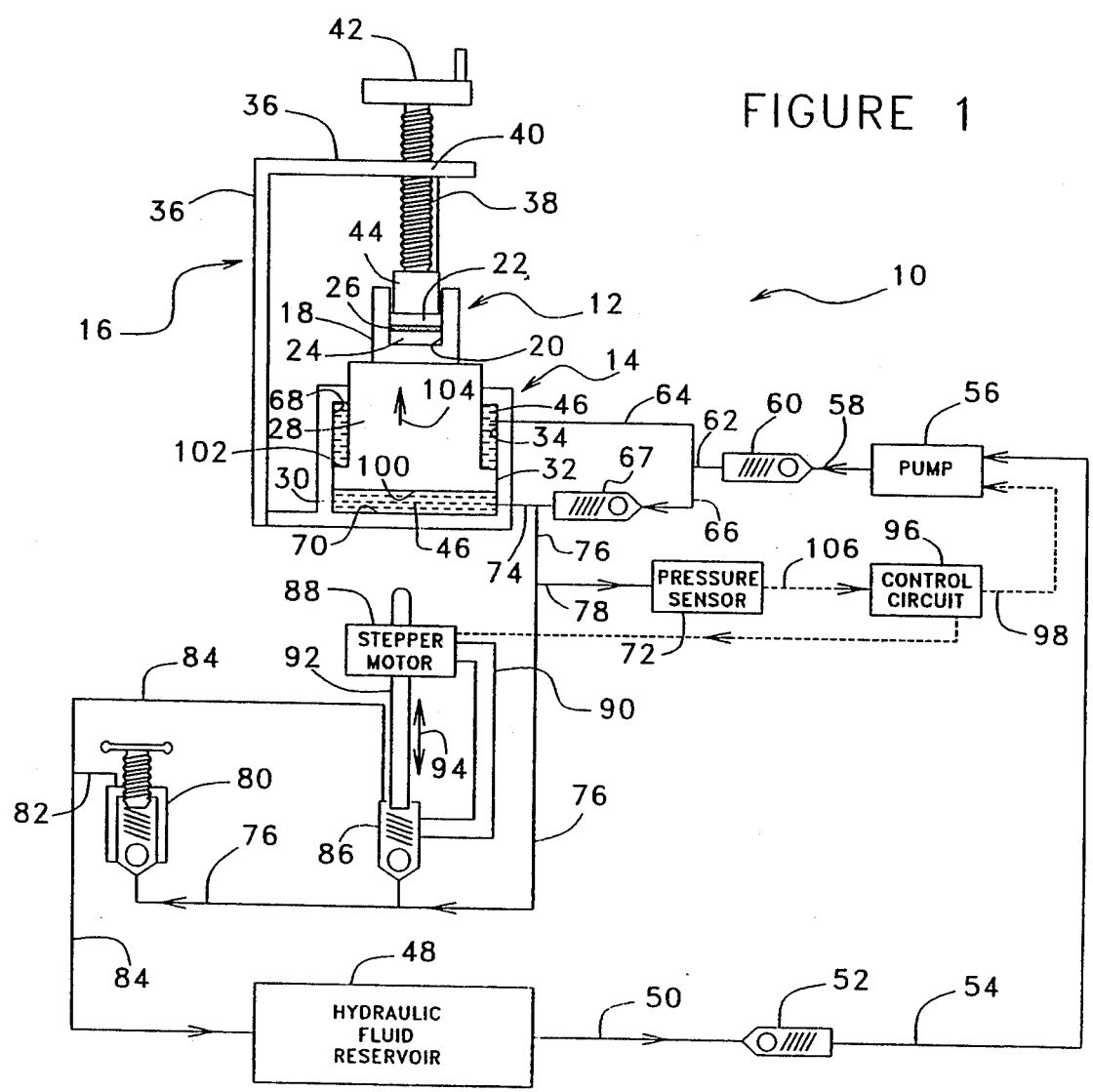
FIG. 1 is a schematic diagram of a pelletizing system constructed in accordance with the present invention.

Referring to FIG. 1, an automatic hydraulic press 10 for carrying out the method of the present invention is illustrated. Press 10 includes a three-part hydraulic die 12, a hydraulic cylinder 14 and an adjustable manual abutment mechanism 16.

Die 12 includes a cylindrical sidewall and base member 18 which, in the illustrated embodiment, defines an inner cavity 20, having the shape of a circular cylindrical volume. An upper die member 22 conformingly fits within cavity 20 as does lower die member 24. During use, a sample of material 26 is contained between the upper and lower die members. Member 18 rests on the hydraulic cylinder 14 which comprises a hydraulic piston 28 and a cylinder member 30. Naturally, the circumferential surface 32 of piston 28 sealingly conforms to the inner sidewall 34 of cylinder member 30.

Die 12 is held in position over hydraulic cylinder 14 by abutment mechanism 16 which generally comprises a support bracket 36 and a threaded operator bar 38 which is mounted in a tapped hole 40 within support bracket 36. A handle 42 is provided for rotation of bar 38 and, accordingly, adjustment of the distance between a compression member 44 and the top of the assembly of die 12 and piston 28, which distance is usually set to be zero in the absence of applied hydraulic pressure within the press 10.

Hydraulic fluid 46, which is present in the various lines and other parts of the hydraulic circuits of the system, is provided from a hydraulic fluid reservoir 48 via a line 50, a one-way valve 52 and a line 54 to a pump 56. The output of pump 56 is sent via a line 58 to a one-way valve 60 which in turn couples its output via lines 62 and 64, and line 66, which is coupled to one way valve 67, to hydraulic cylinder 14 which contains the hydraulic fluid 46 in its upper chamber 68 and its lower chamber 70.

Pressure in the hydraulic cylinder 14 is monitored by a pressure sensor 72 which receives hydraulic fluid via lines 74, 76 and 78. Hydraulic fluid 46 in lower chamber 70 is also coupled by a line 76 to a manually adjusted pressure relief valve 80 whose output is coupled via lines 82 and 84 to hydraulic fluid reservoir 48.

A pressure control valve 86 is also coupled to line 76 to receive the hydraulic fluid 46 in hydraulic cylinder 14 and maintain pressure in hydraulic cylinder 14 by outletting hydraulic fluid through line 84 into reservoir 48 in the event of excess pressure. The pressure at which valve 86 will pass fluid to maintain pressure is adjusted by a stepper motor 88 Which is secured in a fixed position with respect to valve 86 by suitable mechanical structure 90. Stepper motor 88 includes an operator shaft 92 which advances into and out of motor 88 in the directions indicated by arrow 94.

During operation, the operator inputs desired control parameters into control circuit 96. In accordance with the invention such control parameters involve the application of a particular pressure, for example, twenty tons for a period of time, for example, nine seconds and then a gradual bleed-off of pressure to a lower value, finally followed by the complete release of pressure. Actual values will vary for various qualities of various materials, with longer hold times being used for relatively compressible materials and longer times and/or harder pressures used when pellets exhibit textural surfaces or other voids. For example, in the case of compression of a sample of cement, one would apply a pressure of 25 tons for 60 seconds, and allow a 30-second bleed-off to occur down to zero tons and then open the device completely. However, as noted above, the actual time parameters will vary from material to material depending upon the material's consistency, and other factors which can cause a wide divergence in material properties. It is expected that a few trial runs at different pressures and times will result in determination of proper pressing parameters for a particular material of interest to a particular user. Upon the determination by experience of good pressing parameters, the same should be repeated uniformly in order to obtain uniform results.

Upon the input of a particular set of desired parameters at the control circuit 96, control circuit 96 via control line 98 causes pump 56 to begin pumping hydraulic fluid from hydraulic fluid reservoir 48 through valves 52 and 60 into hydraulic cylinder 14. Reverse flow of hydraulic fluid into the pump is prevented by one-way valve 60. Because the area of the underside 100 of piston 28 is far greater than the area of the upper side 102 of piston 28, the application of oil pressure to the upper and lower chambers 68 and 70 of the hydraulic cylinder results in advancing piston 28 in the direction indicated by arrow 104. This results in urging die 12 against abutment or compression member 44 and in the application of pressure to sample 26. The particular pressure achieved is monitored by pressure sensor 72 which acts as a transducer to provide information to the operator in the form of a display as well as to send such information via information line 106 to control circuit 96.

When the desired pressure has been achieved, as detected by sensor 72, this information causes control circuit 96 to stop the operation of pump 56. Back flow of hydraulic fluid 46 from the pump is prevented by one-way valve 52. Precise control of the pressure is achieved by adjustment of stepper motor 88 to a position which results in the setting of valve 86 to a value which results in its ability to maintain a pressure slightly higher than the desired pressure. In the event that excess pressure is obtained, the same will be passed by a line 84 to hydraulic fluid reservoir 48.

Figure 2:
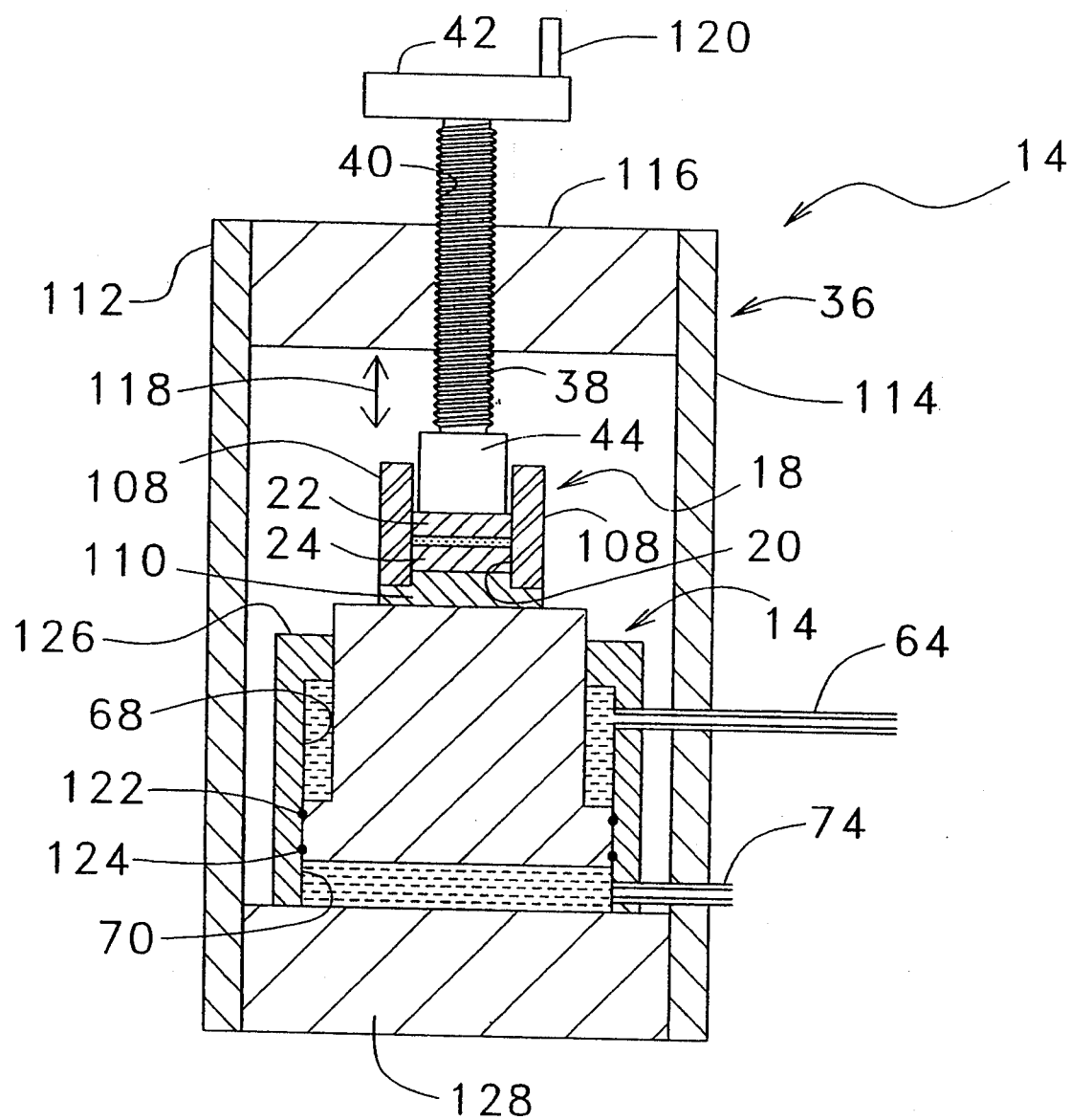
FIG. 2 is a detailed diagrammatic representation of a hydraulic cylinder employed in the system of FIG. 1.

Referring to FIG. 2, a more detailed conceptualized sketch of the hydraulic cylinder 14 is illustrated. This hydraulic cylinder is similar to those in conventional hydraulic compressors presently on the market such as the hydraulic press sold by Spex Industries, Inc. of Edison, N.J. under its catalog number 3624B. In particular, it is noted that member 18 comprises a cylindrical pipe member 108 and a base 110 which fits into pipe member 108 and is secured thereto. Support bracket 36 comprises a pair of side braces 112 and 114 and a top brace 116 secured between them. Bar 38 is mounted in tapped hole 40 and may be moved in the directions indicated by arrow 118 by rotation of handle 42 which may be grasped by the operator by thumb wheel 120. Sealing between upper chamber 68 and lower chamber 70 is provided by an upper annular O-ring seal 122 and a lower annular O-ring seal 124. Cylinder 14 is formed by an upper chamber defining housing 126 and a base 128.

Figure 3:
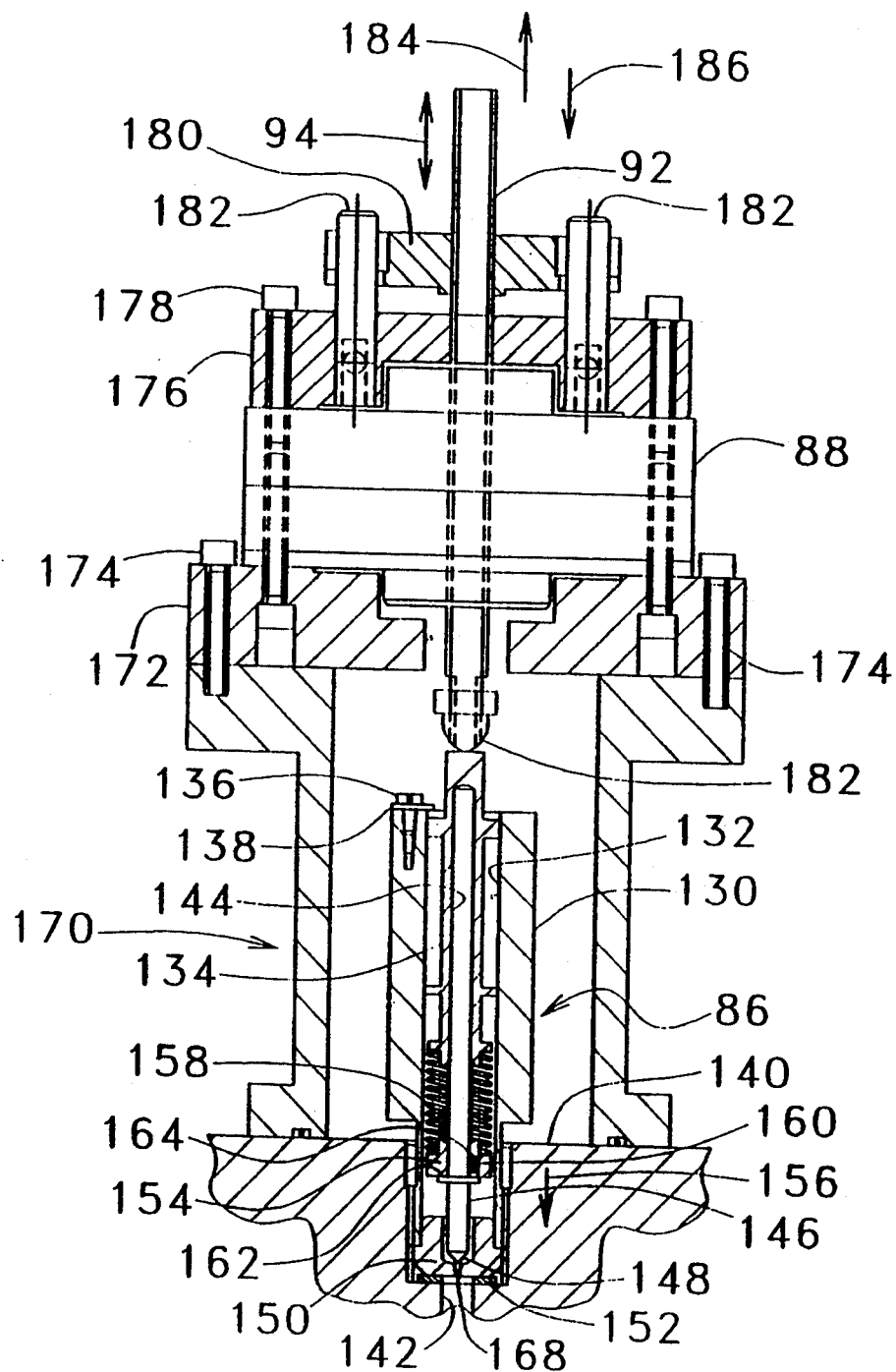
FIG. 3 is a detail of the pressure control subsystem of the inventive pelletizing apparatus.

Referring to FIG. 3, a preferred arrangement for controlling the pressure in press 10 is illustrated. As discussed above, the same includes a pressure control valve 86 and a stepper motor 88. The shaft 92 of motor 88 is advanced in the directions indicated by arrow 94 by forward or reverse actuation of the stepper motor which may be of conventional design. Such a motor is manufactured and sold under catalogue number L92411-Pi by the Airpax Company of Cheshire Industrial Park, Cheshire, Conn. 06410-USA.

Valve 86 comprises a housing 130 which defines an inner bore 132. The backing member or guide 134 fits within bore 132 and is slidably mounted therein. A screw 136 secures a washer 138 in position. Washer 138 prevents guide 134 from exiting housing 130.

Housing 130 is secured to block 140 which includes bore 142, which is coupled to line 76. Guide 134 includes a bore 144 within which a rod 146 is slidably mounted. Rod 146 is terminated in a conical sealing member 148 which sealingly engages a mating surface defined by closure member 150. Closure member 150, in turn is sealingly secured to housing 130 and bore 142. Sealing to bore 142 is provided by rubber washer 152.

Figure 4:
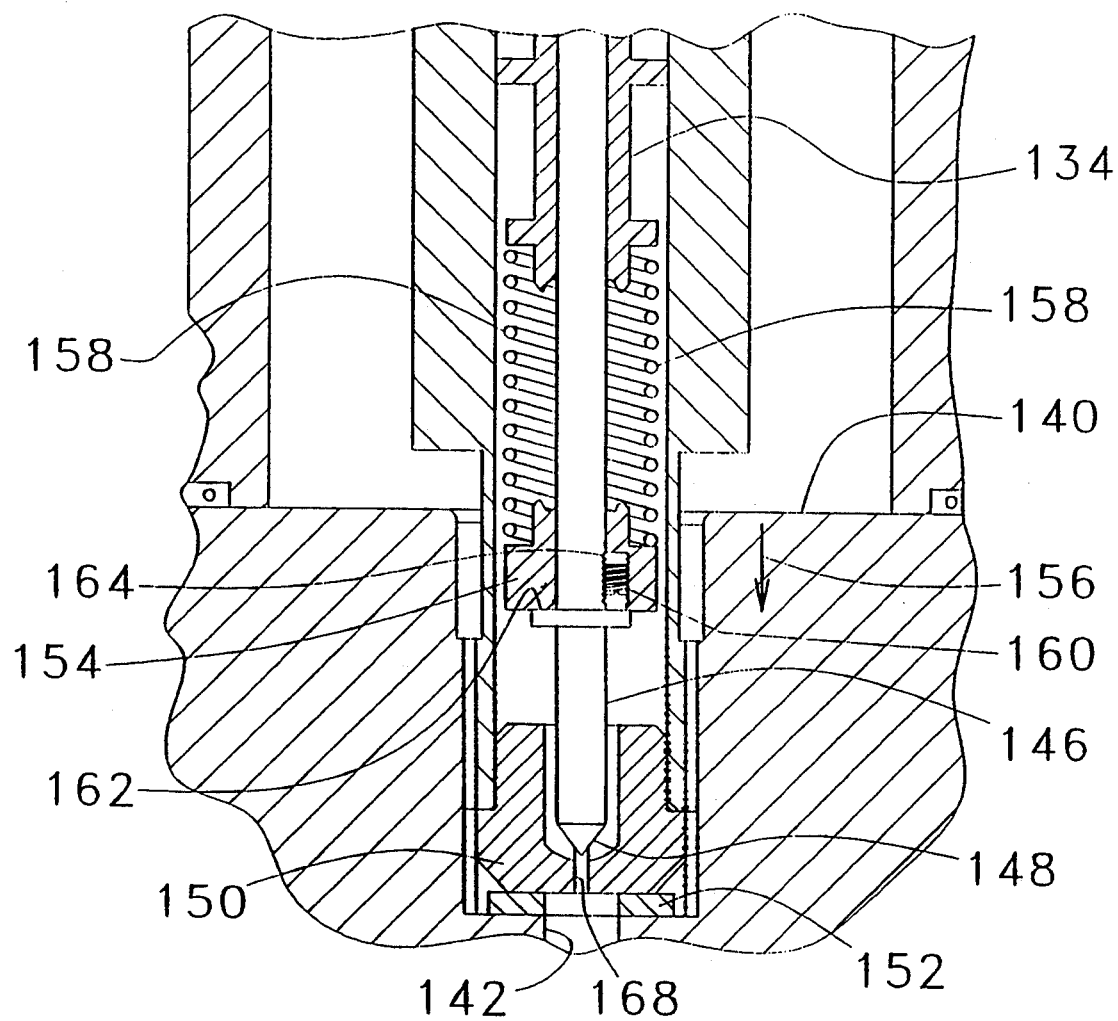
FIG. 4 is a detail of part of FIG. 3.

Referring to FIGS. 3 and 4, stop member 154 is urged in the direction indicated by arrow 156 by a spring 158 which is compressed between the bottom of backing member or guide 134 and stop member 154. The positional relationship between stop member 154 and rod 146 is determined by adjustment of a hex socket screw 160 which is mounted in a hole within stop member 154 and maintained therein by a retainer washer 162, which is also secured to rod 146. The threads in screw 160 matingly engage grooves 164 in rod 146. Thus, rotation of screw 160 results in displacing rod 146 with respect to stop member 154 in the direction indicated by arrow 156. Movement in the opposite direction is achieved by reversal of the direction of rotation of screw 160.

As can be seen from the above, the application of excess pressure to the hydraulic fluid in bore 142 will result in the displacement of the sealing member 148 from the seat of closure in the closure member 150 and the transmission of hydraulic fluid through bore 168 in closure member 150. The amount of pressure necessary to result in such a flow of oil through bore 168 is a function of the compression of spring 158. This, in turn, is a function of the distance between the guide 134 and the stop member 154 which, in turn, is a function of the position of guide 134 in bore 132.

This position is controlled in accordance with the preferred embodiment, by lateral movement of shaft 92 of stepper motor 88 which is secured with respect to pressure control valve 86 by a support 170 and a base plate 172 which are secured to each other by bolts 174. Additional rigidity is given to the system by a back support for the end of shaft 92 which comprises a backing plate 176 secured to stepper motor 88 by bolts 178.

Yet additional support is provided by tip guiding plate 180 which is maintained in position by a pair of support posts 182 which, in turn, are secured to backing plate 176. Finally, the tip of shaft 92 is provided with a rounded contacting member 182 which improves the position of the system by providing for a substantially only a point of contact with guide 134.

In accordance with the preferred embodiment of the invention, shaft 92 is advanced toward valve 86 to the extent necessary to provide pressure relief at a value substantially identical to that which one desires to press. This is ensured on the basis of information stored in control circuit 96 and which provides rough information on this and is controlled more finely by information detected by pressure sensor 72. When pressure at the desired value is achieved, the same is held for a period of time, which the human operator has input into the control circuit. If pressure should fall during this period of time, the pump is turned on. At the same time, the position of shaft 92 can be used to vary the maximum pressure which valve 86 will permit.

In accordance with an alternative embodiment of the system of the present invention, pump 56 can be turned on continuously and valve 86 used to continuously keep the pressure at the maximum value. In the event of a failure of valve 86 or other parts of the system, maximum overload protection is provided by valve 80.

In accordance with the present invention, pressure regulated by valve 86 is not reduced by simple motion of shaft 92 of the stepper motor in the direction indicated by arrow 184. Rather, movement is made in the direction of arrow 184 by a number of steps insufficient to produce the value at which one wishes pressure relief to occur in valve 86. The control circuit 96 then causes the shaft to move a fewer number of steps in the direction of arrow 186, followed by the larger number of steps in the direction of arrow 184 and so forth repeating the process resulting in several steps of forward movement, fewer steps of backward movement and a net release of spring force and ultimately pressure release or adjustment to a lower pressure, but without the problem of abrupt pressure changes which characterized and complicated the operation of prior art systems.

In accordance with the present invention, the stepper motor is driven at a rate of about 250-750 hertz. Between 20 and 5 steps out are followed by a lesser number of steps in the opposite direction.

In accordance with the preferred embodiment, it has been found that if the stepper motor referred to above is used, nineteen steps in the direction of arrow 184 followed by twelve in the direction of arrow 186 has been found to yield satisfactory results. Likewise, it has been found desirable to bleed pressure to an intermediate value, for example, a value of twenty percent lower than the highest value in a compression cycle by a gradual linear movement of the stepping motor. This linear movement is begun after the initial high pressure is released, for example, to a value 98% of the high pressure. Linear movement may be controlled to extend over any period of time. Such linear movement may be a net linear movement resulting from movement in opposite directions of the stepper motor shaft, as described above.

Broadly stated, the present invention provides a programmable hydraulic press for automated, repetitive pressing of sample pellets comprising:

a) a die cavity to receive a sample of compressible material;

b) a die member mounted for movement in relation to said die cavity to compress said sample into a pellet;

c) cyclically operable and depressurizable hydraulic pressurization means to effect said movement between said die cavity and die member and effect compression of said sample;

d) a manually settable hydraulic control circuit for said hydraulic pressurization means to actuate said cyclic operation and provide a pellet-compression cycle having the following parameters:
 i) a compression step of predetermined duration at a preselected working pressure; and
 ii) a bleed-down step wherein said preselected working pressure is bled down over a preselected bleed-down time;

said control circuit further including data input means for manually effected operator inputs of said preselected working pressure and bleed-down time whereby said press is operable automatically to compress samples into pellets at said preselected working pressure and to relieve said pressure over said preselected bleed-down time.

While an illustrative embodiment of the invention has been described above, it is, of course, understood that various modifications will be apparent to those of ordinary skill in the art. Such modifications are within the spirit and scope of the invention, which is limited and defined only by the appended claims.

We claim:

1. Sample pelletization apparatus for compressing a sample by hydraulic pressure said apparatus including automated pressure control means and comprising:
 a) a die for receiving said sample in compressible form;
 b) an abutment for holding said sample in a fixed position against said hydraulic pressure;
 c) hydraulic piston-and-cylinder means positioned to drive said die in a direction toward said abutment;
 d) a pump for feeding hydraulic fluid to pressurize said piston-and-cylinder means to a working pressure; and
 e) a pressure control valve coupled to said piston-and-cylinder means for controlling the working pressure in said hydraulic cylinder, said pressure control valve comprising:
  i) a sealing member;
  ii) a valve seat defining an outlet configured, dimensioned and positioned to engage said sealing member with said sealing member closing said outlet;
  iii) compressible spring means urging said sealing member towards said seat to close said outlet;
  iv) a backing member putting said spring means under compression by maintaining a distance between said backing member and said seat;
  v) mechanical structure for adjusting said distance to actuate said pressure control valve; and
 f) manually settable control circuit means for said mechanical structure said control circuit means being connected with said backing member to effect control of said pressure control valve and including means to receive operator inputs of desired relief pressure and desired bleed-down time.

2. Apparatus according to claim 1, wherein said mechanical structure comprises a stepper motor rigidly mounted with respect to said seat, said stepper motor having a shaft engageable with said sealing member and indexable to move said sealing member toward and away from said valve seat whereby the compression of said spring means is adjustable.

3. A programmable hydraulic press for automated, repetitive pressing of sample pellets comprising:
 a) a die cavity to receive a sample of compressible material;
 b) a die member mounted for movement in relation to said die cavity to compress said sample into a pellet;
 c) cyclically operable and depressurizable hydraulic pressurization means to effect said movement between said die cavity and die member and effect compression of said sample;
 d) a manually settable hydraulic control circuit for said hydraulic pressurization means to actuate said cyclic operation and provide a pellet-compression cycle having the following parameters:
  i) a compression step of predetermined duration at a preselected working pressure; and
  ii) a bleed-down step wherein said preselected working pressure is bled down over a preselected bleed-down time;

said control circuit further including data input means for manually effected operator inputs of said preselected working pressure and bleed-down time whereby said press is operable automatically to compress samples into pellets at said preselected working pressure and to relieve said pressure over said preselected bleed-down time.

4. A programmable press according to claim 3 wherein said hydraulic pressurization means comprises hydraulic piston-and-cylinder means coupled between said die cavity and die member and a pressure controlled relief valve, said relief valve being settable to said preselected pressure and openable to permit bleed down of said preselected working pressure.

5. A programmable press according to claim 4 comprising mechanical relief valve adjustment means acting on said relief valve to control said setting and opening thereof.

6. A programmable press according to claim 5 programmed for said control circuit means to actuate said adjustment means to an extent insufficient to permit the desired pressure relief, and to retract said adjustment means and repeat the cycle in a progressive manner to effect smooth, non-surging pressure relief.

7. A programmable press according to claim 4 comprising a second pressure relief valve for relief of overpressure in said piston-and-cylinder means said second pressure relief valve being connected in parallel with first said pressure relief valve and being operative as a safety valve.

8. Sample pelletization apparatus for compressing a sample by hydraulic pressure said apparatus including automated pressure control means and comprising:
 a) a die for receiving said sample in compressible form;
 b) an abutment for holding said sample in a fixed position against said hydraulic pressure;
 c) hydraulic piston-and-cylinder means positioned to drive said die in a direction toward said abutment;
 d) a pump for feeding hydraulic fluid to pressurize said piston-and-cylinder means to a working pressure; and
 e) a pressure control valve coupled to said piston-and-cylinder means for controlling the working pressure in said hydraulic cylinder, said pressure control valve comprising:

i) a sealing member;

ii) a valve seat defining an outlet configured, dimensioned and positioned to engage said sealing member with said sealing member closing said outlet;

iii) compressible spring means for urging said sealing member towards said seat, closing said outlet;

iv) a backing member putting said spring means under compression by maintaining a distance between said backing member and said seat;

v) mechanical structure for adjusting said distance to actuate said pressure control valve, said mechanical structure comprising a stepper motor rigidly mounted with respect to said seat, said stepper motor having a shaft engageable with said sealing member and indexable to move said sealing member toward and away from said valve seat whereby the compression of said spring means is adjustable;

f) means for detecting the pressure of hydraulic fluid in said hydraulic cylinder and means for controlling said stepper motor in response thereto; and g) manually settable control circuit means programmed to cause said shaft of said stepper motor to pull away in a first direction from said seat by a first number of steps which is less than that needed to cause a desired change in said working pressure in the hydraulic cylinder and then proceed in a second direction opposite to said first direction a second number of steps smaller than said first number of steps and then alternate in the first direction and the second direction with numbers of steps resulting in net movement in a desired direction, said control circuit being programmed to cause said shaft to alternately move in said first direction and in said second direction until pressure is reduced to a desired value.

9. Apparatus as in claim 8, wherein said control circuit is programmed to effect said release of pressure by alternately advancing and retracting the shaft of said stepper motor over a fixed period of time.

10. A programmable hydraulic press for the repetitive pressing of sample pellets comprising:

a) die cavity to receive a sample of compressible material;

b) a die member movable in said die cavity to compress said sample into a pellet;

c) hydraulic piston-and-cylinder means coupled to said die member to actuate said die and effect compression of said sample;

d) hydraulic circuit means connected to said piston-and-cylinder means to pressurize said piston-and-cylinder to a working pressure and to depressurize said piston-and-cylinder;

e) a pressure controlled relief valve to control said working pressure, said relief valve being settable to a predetermined relief pressure, openable to permit bleed down of said working pressure and comprising a valve sealing member and valve seat, said valve seat defining an outlet configured, dimensioned and positioned to engage said sealing member with said sealing member closing said outlet;

f) relief valve adjustment means controllable to set said predetermined relief pressure and to open said relief valve to provide controlled bleed down, said valve adjustment means including i) adjustable compressible spring means urging said sealing member towards said seat to interengage and close said outlet;

ii) a backing member movable to adjust said compression spring means, said backing member putting said spring means under compression by maintaining a distance between said backing member and said seat; and iii) a mechanical structure for adjusting said distance to actuate said pressure control valve, said mechanical structure comprising a stepper motor rigidly mounted with respect to said seat, said stepper motor having a shaft engagable with said sealing member and indexable to move said sealing member toward and away from said valve seat whereby the compression of said spring means may be adjusted;

g) a control circuit for actuating said relief valve adjustment means, said control circuit being programmed to:

i) receive operator inputs of desired relief pressure and desired bleed-down time;

ii) provide a predetermined press duration at said working pressure;

iii) cause said shaft of said stepper motor to pull away in a first direction from said seat by a first number of steps which is less than that needed to cause a desired change in said working pressure in the hydraulic cylinder and then proceed in a second direction opposite to said first direction a second number of steps smaller than said first number of steps and then alternate in the first direction and the second direction with numbers of steps resulting in net movement in a desired direction, said control circuit being programmed to cause said shaft to alternately move in said first direction and in said second direction until pressure is reduced to a desired value; and iv) advance the backing member in one direction and to retract it in an opposite direction, said advancing or retracting comprising:

a) one or more cycles of a plurality of incremental steps in the desired advancing or retracting direction followed by a lesser number of similar incremental steps in the opposite direction;

whereby, said press is operable automatically to compress samples into pellets at a predetermined operator-selectable working pressure and to release said working pressure with a predetermined operator-selectable bleed-down time.

11. A programmable press according to claim 10 wherein said control circuit is programmed to effect said release of pressure by alternately advancing and retracting the shaft of said stepper motor over a fixed period of time.

* * * * *